(12) United States Patent
Crary et al.

(10) Patent No.: US 10,143,404 B2
(45) Date of Patent: Dec. 4, 2018

(54) SYSTEMS AND METHODS FOR AUTOMATICALLY DETERMINING PATIENT SWALLOW FREQUENCY

(75) Inventors: Michael Allen Crary, Gainesville, FL (US); Giselle D. Carnaby-Mann, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 473 days.

(21) Appl. No.: 13/817,206

(22) PCT Filed: Nov. 16, 2011

(86) PCT No.: PCT/US2011/061001
§ 371 (c)(1),
(2), (4) Date: Feb. 15, 2013

(87) PCT Pub. No.: WO2012/068254
PCT Pub. Date: May 24, 2012

(65) Prior Publication Data
US 2013/0245499 A1 Sep. 19, 2013

Related U.S. Application Data

(60) Provisional application No. 61/414,597, filed on Nov. 17, 2010.

(51) Int. Cl.
*A61B 5/11* (2006.01)
*A61B 5/00* (2006.01)
(Continued)

(52) U.S. Cl.
CPC .......... *A61B 5/1107* (2013.01); *A61B 5/0002* (2013.01); *A61B 5/4205* (2013.01); *A61B 7/04* (2013.01); *A61B 7/00* (2013.01)

(58) Field of Classification Search
CPC .. A61B 7/003; A61B 7/04; A61B 7/00; A61B 5/037; A61B 5/42; A61B 1/041
(Continued)

(56) References Cited

U.S. PATENT DOCUMENTS

| 5,954,673 A | 9/1999 | Stachlin et al. |
| 6,551,256 B1 | 4/2003 | Stasz et al. |

(Continued)

FOREIGN PATENT DOCUMENTS

| JP | 9248282 | 9/1997 |
| JP | 2005304890 A | 11/2005 |
| JP | 2005263299 A | 10/2006 |

OTHER PUBLICATIONS

Cichero, Julie, et al., "Acoustic Signature of the Normal Swallow: Characterization by Age, Gender, and Bolus Volume," 2002, Ann Otol Rhinol Laryngol, 111, 623-632.*

(Continued)

*Primary Examiner* — Daniel Cerioni
(74) *Attorney, Agent, or Firm* — Polsinelli PC

(57) ABSTRACT

Patient swallow frequency is automatically determined by collecting patient data, analyzing the patient data to automatically identify swallow events, and automatically calculating the swallow frequency based upon the identified swallow events. In some cases, the patient data is collected by a patient interface that wirelessly transmits the data to a computing device for analysis.

10 Claims, 4 Drawing Sheets

(51) Int. Cl.
*A61B 7/04* (2006.01)
*A61B 7/00* (2006.01)

(58) Field of Classification Search
USPC .................................. 600/586, 587, 593
See application file for complete search history.

(56) References Cited

U.S. PATENT DOCUMENTS

| | | | |
|---|---|---|---|
| 7,433,484 | B2 | 10/2008 | Asseily et al. |
| 2005/0283096 | A1* | 12/2005 | Chau ..................... A61B 5/11 600/593 |
| 2006/0030794 | A1 | 2/2006 | Nation et al. |
| 2006/0084380 | A1 | 4/2006 | Hoyt et al. |
| 2006/0155205 | A1* | 7/2006 | Sotos ................. A61B 5/4806 600/529 |
| 2006/0282010 | A1* | 12/2006 | Martin ................ A61B 5/4205 600/560 |
| 2008/0264180 | A1 | 10/2008 | Gakhar et al. |
| 2008/0306373 | A1* | 12/2008 | Kandori ............. A61B 5/1126 600/407 |
| 2009/0018409 | A1* | 1/2009 | Banet .................. A61B 5/0408 600/301 |
| 2009/0022350 | A1 | 1/2009 | Asseily et al. |
| 2009/0024004 | A1 | 1/2009 | Yang |
| 2010/0106027 | A1 | 4/2010 | Jaeger |
| 2010/0217102 | A1* | 8/2010 | LeBoeuf ................ A61B 5/00 600/310 |
| 2011/0034831 | A1* | 2/2011 | Christensen ........ A61B 5/0002 600/586 |
| 2011/0160615 | A1* | 6/2011 | Matsumura .......... A61B 5/4205 600/587 |
| 2012/0046641 | A1* | 2/2012 | Jedwab ................... A61B 5/00 604/503 |

OTHER PUBLICATIONS

International Preliminary Report on Patentability dated May 30, 2013.
International Search Report and Written Opinion dated Jul. 18, 2012.
Sazonov, et al., "Non-Invasive Monitoring of Chewing and Swallowing for Objective Quantification of Ingestive Behavior," Physiological Measurement, vol. 29, No. 5, Apr. 22, 2008.
Aydogdu, et al., "Electrodiagnostic Methods for Neurogenic Dysphagia," Electroencephalography and Clinical Neurophysiology/Electromyigraphy and Motor Control, vol. 109, Issue 4, Aug. 1998, Abstract.

* cited by examiner

SYSTEMS AND METHODS FOR AUTOMATICALLY DETERMINING PATIENT SWALLOW FREQUENCY

CROSS-REFERENCE TO RELATED APPLICATION(S)

This application is the 35 U.S.C. § 371 national stage of PCT application PCT/US2011/061001, filed Nov. 16, 2011 which claims priority to and the benefit of U.S. Provisional Application Ser. No. 61/414,597, filed Nov. 17, 2010, both of which are hereby incorporated by reference herein in their entirety.

BACKGROUND

Stroke is the leading cause of disability among adults in the United States. Dysphagia has been reported to impact as many as 65% of acute stroke patients. Dysphagia has a negative impact on long-term functional outcome, and increases the risk of under nutrition and pneumonia, both of which have been related to increased mortality. Early identification of dysphagia in stroke survivors has been shown to have a direct benefit for reduced morbidity and mortality. Early treatment for dysphagia in stroke patients has been shown to improve swallowing ability, reduce dysphagia-related morbidity and to improve nutritional status. Therefore, early identification of dysphagia in the stroke survivor can have a significant impact not only on the patient's survival and quality of life, but also on the use of health care resources and associated costs.

Currently, identification of dysphagia in patients with acute stroke is accomplished via screening protocols early in the post-stroke admission period. Although several clinical investigators have offered a variety of dysphagia screening protocols, none have developed a sufficiently valid and inexpensive dysphagia screening method for patients in the acute phase of stroke. Furthermore, no consensus method has emerged regarding the most effective screening tool. Finally, available evidence suggests that no published screening protocol has reported adequate sensitivity and specificity to function as an effective dysphagia screening tool in stroke.

In view of the above discussion, it can be appreciated that it would be desirable to have a system and method for identifying dysphagia.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, dysphagia often affects stroke patients and can have a negative impact on the patient, including increased likelihood of death. Although several clinical investigators have offered a variety of dysphagia screening protocols, none have developed a sufficiently valid and inexpensive dysphagia screening method and no consensus method has emerged. Disclosed herein are systems and methods for automatically determining patient swallow frequency that can be used to diagnose dysphagia. In one embodiment, a system includes a patient interface in the form of device that adheres to the neck of the patient and wirelessly transmits sensed data to a separate computing device for analysis. The computing device then automatically identifies and counts patient swallows for the purpose of determining the patient's swallow frequency. In some embodiments, the computer further identifies the likelihood of the patient suffering from dysphagia based upon the determined swallow frequency.

In the following disclosure, various embodiments are described. It is to be understood that those embodiments are example implementations of the disclosed inventions and that alternative embodiments are possible. All such embodiments are intended to fall within the scope of this disclosure. Furthermore, although the systems and methods are described as being used to diagnose dysphagia, for example in stroke patients, it is noted that this is just one example application for the systems and methods. All other applications are intended to fall within the scope of this disclosure.

Figure 1:
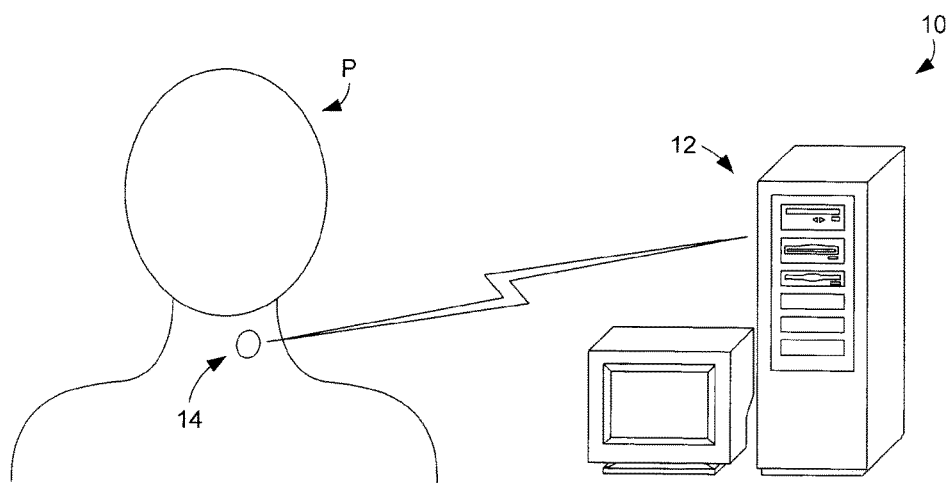
FIG. 1 is a schematic view of an embodiment of a system for automatically determining patient swallow frequency.

FIG. 1 illustrates an embodiment of a system for automatically determining patient swallow frequency. As is shown in FIG. 1, the system 10 can include a computing device 12 and a patient interface 14. In some embodiments, the patient interface 14 comprises an adhesive monitoring device that, as is illustrated in FIG. 1, can be adhered to the neck of a patient, P. By way of example, the patient interface is attached at a point on the adjacent over the lateral border of the trachea immediately inferior to the cricoid cartilage. Although the patient is represented in FIG. 1 as a human patient, it is to be noted that it is possible for the interface 14 and the system 10 to be used with non-human patients.

With further reference to FIG. 1, the computing device 12 can take the form of a conventional computer, such as a desktop computer. It is noted, however, that any computing device that can analyze the data collected by the patient interface 14 can be used. Therefore, the computing device 12 can instead be a portable computing device, such as a notebook (laptop) computer, a tablet computer, or a hand-held computer. Furthermore, the computing device 12 can comprise a purpose built device for making swallow frequency determinations.

Figure 2:
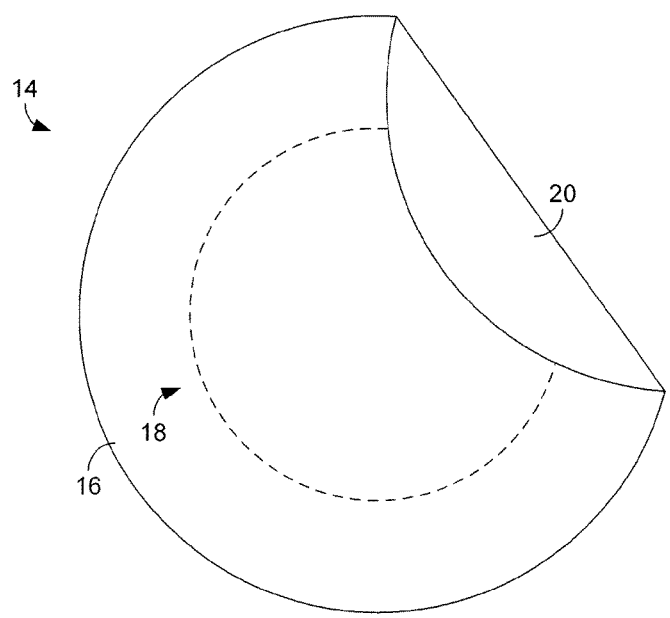
FIG. 2 is a top view of an embodiment of a patient interface that can be used in system of FIG. 1.

FIG. 2 depicts an example configuration for the patient interface 14. As shown in FIG. 2, the patient interface 14 can comprise an outer substrate 16 to which electronic components (described in relation to FIG. 3 and generally identified by reference numeral 18) are mounted or otherwise connected. In some embodiments, the substrate 16 can be composed of a thin, flexible polymeric material similar to that used with common adhesive bandages. The substrate 16 can have a circular outer periphery and have a diameter in the range of approximately 0.25 to 2 inches. The inner surface 20 of the substrate 16 is provided with a layer of pressure-sensitive adhesive that enables the patient interface 14 to adhere to the patient's skin and be used as a one-time-use patch. The electronic components 18 can be positioned at the center of the patient interface 14 spaced from the outer periphery of the substrate 16.

Figure 3:
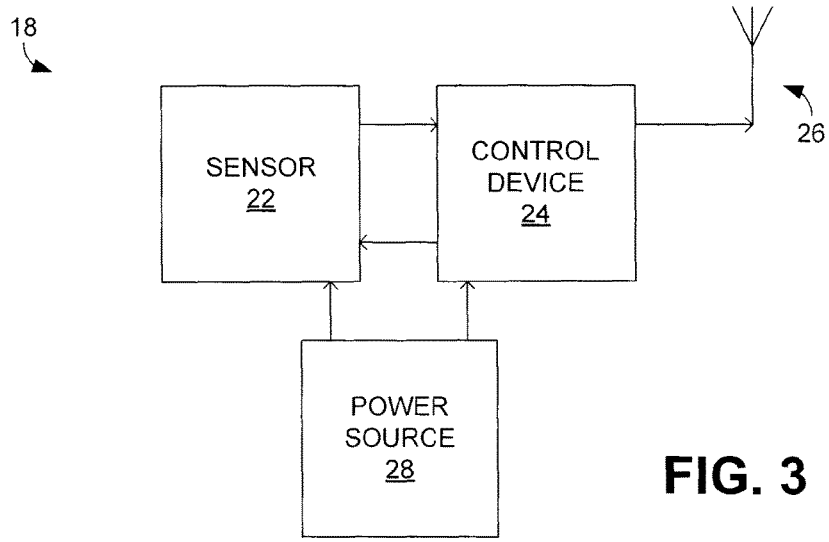
FIG. 3 is a block diagram of an embodiment of electronic components of the patient interface of FIG. 2.

FIG. 3 shows example electronic components 18 that can be comprised by the patient interface 14. In the illustrated embodiment, the components 18 include a sensor 22, a control device 24, and a power source 28. The sensor 22 is configured to collect data indicative of patient swallows and, for example, can be configured as an acceleration or pressure sensor. In some embodiments, the sensor 22 comprises an accelerometer that senses or measures accelerations associated with movement of patient tissues when the patient swallows. In other embodiments, the sensor 22 comprises a microphone that senses sounds associated with the patient swallowing. In some embodiments, only the data collected by the single sensor 22 is used to make the swallow frequency determination and the system 10 comprises no other sensors.

The control device 24 controls the overall operation of the patient interface 14 and is further configured to transmit data collected by the sensor 22 to the computing device 12. By way of example, the sensor control device 24 comprises a microprocessor that is configured to wirelessly transmit data using an antenna 26, which can comprise a circuit board antenna. Wireless communication can be achieved using any suitable wireless protocol. Possible wireless protocols include short-range radio frequency (RF) wireless protocols such as WiFi (IEEE 802.11) as well as Bluetooth and ZigBee (IEEE 802.15). Although wireless communications have been explicitly identified, it is noted that the data collected by the sensor 22 can alternatively be transmitted to the computing device 12 using a wired connection, such as a universal serial bus (USB) connection.

As is further depicted in FIG. 3, the electrical components further include an onboard power source 28. By way of example, the power source 28 can be a 3 volt (V) battery that can provide power necessary to operate the components of the patient interface 14 for approximately four hours.

Figure 4:
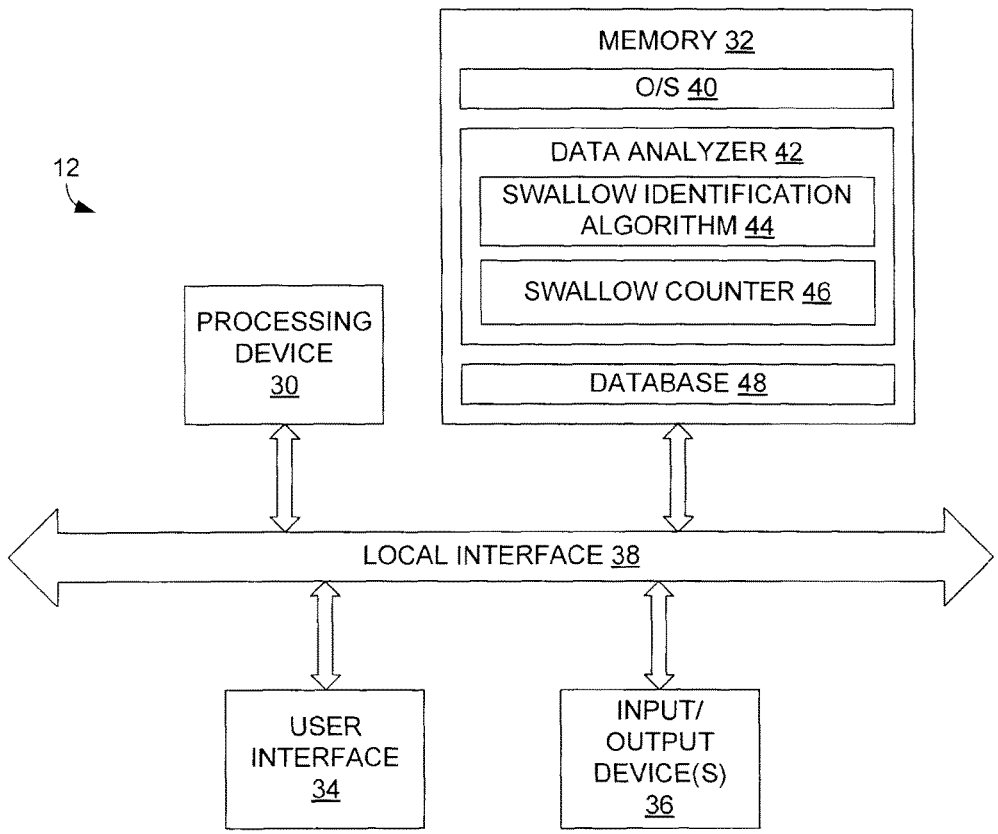
FIG. 4 is a block diagram of an embodiment of a computing device shown in FIG. 1.

FIG. 4 illustrates an example embodiment for the computing device 12 shown in FIG. 1. As indicated in that FIG. 4, the computing device 12 comprises a processing device 30, memory 32, a user interface 34, and at least one input/output (I/O) device 36, each of which is connected to a local interface 38.

The processing device 30 can comprise a central processing unit (CPU) that controls the overall operation of the computing device 12. The memory 32 includes any one of or a combination of volatile memory elements (e.g., RAM) and nonvolatile memory elements (e.g., hard disk, ROM, etc.) that store code that can be executed by the processing device 30 during image analysis.

The user interface 34 comprises the components with which a user interacts with the computing device 12. The user interface 34 can comprise one or more conventional computer interface devices, such as a keyboard, a mouse, monitor, and touch screen. The one or more I/O devices 36 are adapted to facilitate communications with other devices and may include one or more communication components such as a modulator/demodulator (e.g., modem), wireless (e.g., radio frequency (RF)) transceiver, network card, etc.

The memory 32 (i.e., a non-transitory computer-readable medium) comprises various programs (i.e., logic) including an operating system 40 and a data analyzer 42. The operating system 40 controls the execution of other programs and provides scheduling, input-output control, file and data management, memory management, and communication control and related services. The data analyzer 42 is configured to receive patient data collected by the patient interface 14 and analyze that data for the purpose of automatically determining patient swallow frequency. As is shown in FIG. 4, the data analyzer 42 can include a swallow identification algorithm 44 and a swallow counter 46 that together can be used to automate the swallow frequency determination.

Also comprised by the memory 32 is a database 48 that can store model swallow data for comparison with the patient data. In some embodiments, the swallow data in the database 48 can be associated with patient parameters that may have an effect on swallow frequency, such as age, sex, or health.

Various code (i.e., logic) has been described in this disclosure. Such code can be stored on any computer-readable medium for use by or in connection with any computer-related system or method. In the context of this document, a "computer-readable medium" is an electronic, magnetic, optical, or other physical device or means that contains or stores code, such as a computer program, for use by or in connection with a computer-related system or method.

Figure 5:
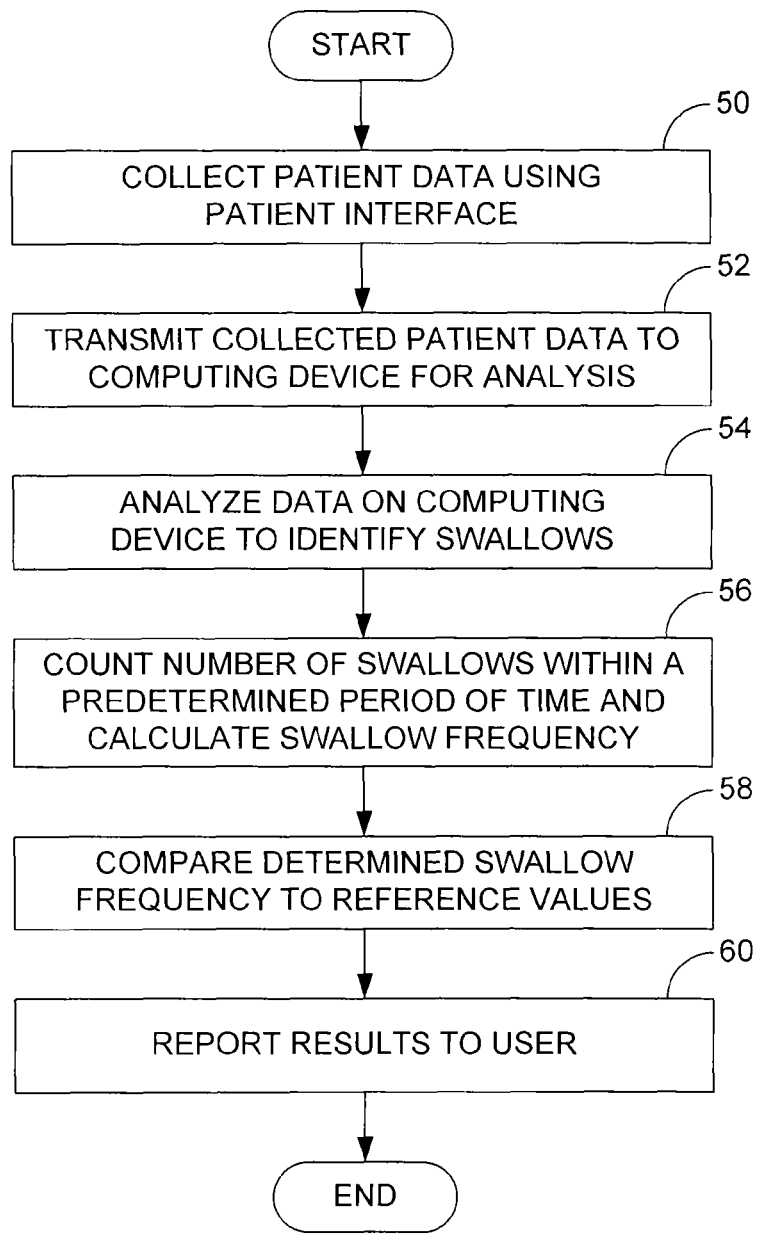
FIG. 5 is a flow diagram of a first method for automatically determining patient swallow frequency.

FIG. 5 describes an example embodiment of a method for automatically determining patient swallow frequency that can, for example, be performed by the system 10 of FIG. 1. Beginning with block 50, patient data is collected using the patient interface. In some embodiments, the patient data comprises either acceleration data collected by the accelerometer or pressure data collected by the microphone. Regardless of its nature, the patient data will contain features that are indicative of the occurrence of a swallow.

With reference to block 52, the collected patient data is transmitted to the computing device for analysis. As indicated above, the data can be wirelessly transmitted to the computing device by the patient interface. Alternatively, however, the data can be transmitted to the computing device via a wire or cable.

Once the data is received by the computing device, the data can be analyzed to identify swallows, as indicated in block 54. By way of example, the analysis is conducted by executing the swallow identification algorithm of the data analyzer on the computing device. Significantly, swallows are automatically identified by the computing device without human assistance (e.g., identifying or verifying swallow events).

Referring next to block 56, the number of swallows within a predetermined period of time are counted and the swallow frequency is calculated. By way of example, the counting and frequency determination are performed by the swallow counter of the computing device.

At this point, the determined swallow frequency can be compared to reference data, as indicated in block 58. In some cases, the reference data to which the patient data is compared can be reference data associated with patient parameters that the patient possesses (e.g., age, sex, etc.). Once the comparison has been performed, the results of the comparison can be reported to the user. In some cases, the results can include the diagnosis of a particular condition. For example, if it was determined that the patient exhibits a relatively low swallow frequency, a dysphagia diagnosis could be reported.

Figure 6:
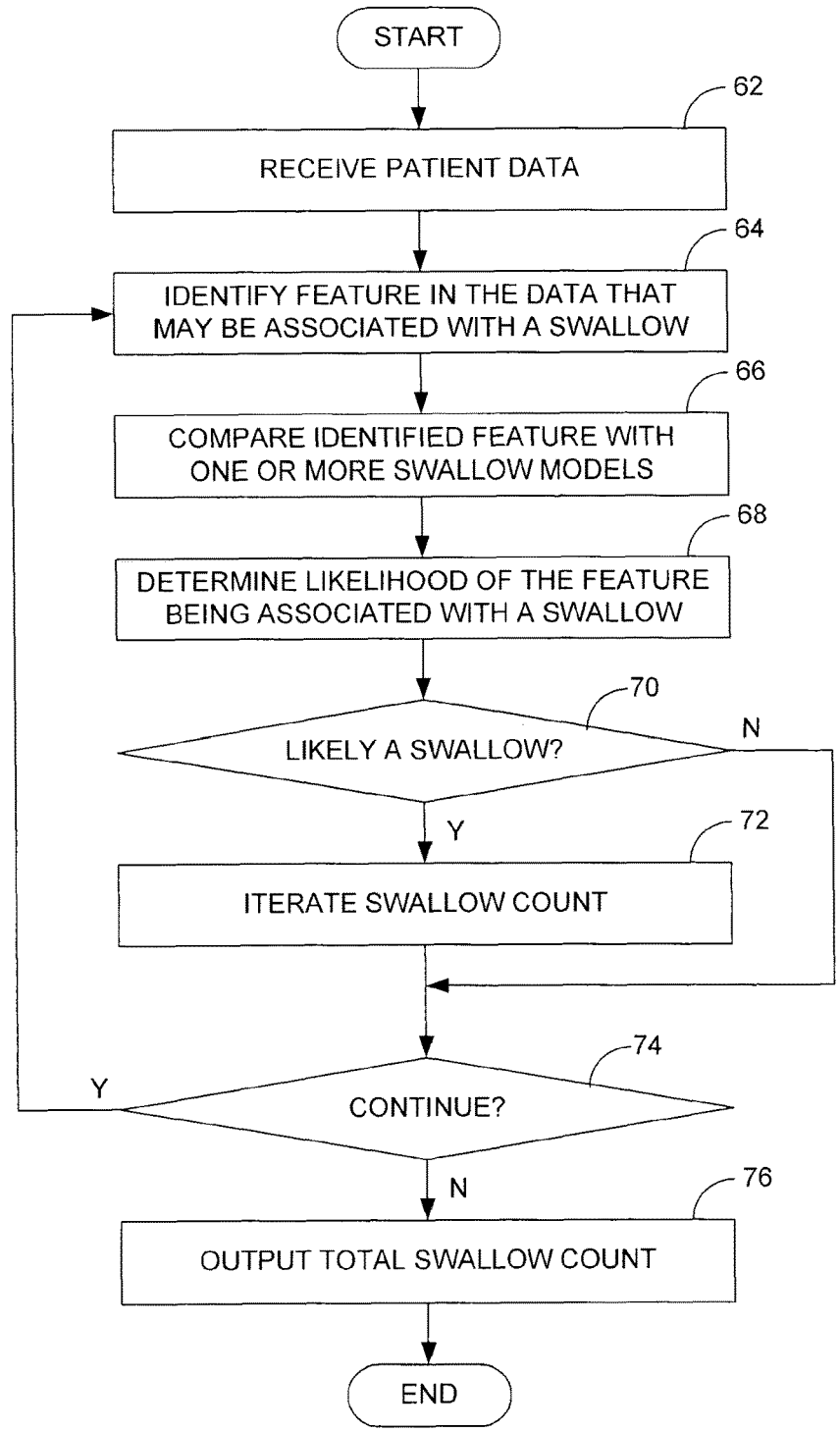
FIG. 6 is a flow diagram of a second method for automatically identifying patient swallows.

FIG. 6 describes an example method for automatically identifying patient swallow frequency. By way of example, the method can be practiced by the data analyzer described above in relation to FIG. 4 over a predetermined duration of time. Beginning with block 62, the collected patient data is received. The data can then be analyzed to identify a feature in the data that may be associated with a swallow event, as indicated in FIG. 64. Features within the data can be any collection of data that is potentially associated with a swallow. For example, if the patient data is acoustic data, identified features may be data having particular frequencies, amplitudes, and/or time durations that are typically observed when a patient swallows. In some embodiments, appropriate filters can be used to reduce the amount of data that is considered.

After a feature has been identified, the feature can be compared with one or more model swallow data that is representative of data that is typically observed when a patient swallows, as indicated in block 66. Depending upon the nature of the sensor that is used to collect the patient data, the model swallow data can comprise acceleration data or pressure data. Through that comparison, the likelihood of the feature being associated with a swallow can be determined, as indicated in block 68. As mentioned above, the swallow occurrence determination can be made in view of only the information collected by the single sensor. Therefore, only a single channel of data is used to identify swallows.

Flow from this point depends upon whether the feature is determined to be likely associated with a swallow or not (see decision block 70). If so, a swallow count is iterated, as indicated in block 74. In not, the swallow count is not iterated. As indicated in decision block 74, flow next depends upon whether further analysis is to be performed. If so, flow returns to block 64 and the next feature within the data is identified. If not, meaning that each feature in the data for the predetermined period of time has been identified and analyzed, flow continues to block 76 at which a total swallow count is output. As mentioned above, a diagnosis (e.g., dysphagia or not) can be output based upon the number of swallows observed in the predetermined time period (i.e., the swallow frequency).

The invention claimed is:

1. A method for determining a frequency of spontaneous patient swallowing and diagnosing dysphagia in the patient, the method comprising:
    continuously collecting spontaneous patient swallow data using a patient interface monitoring device positioned in contact with a neck of a patient, the patient interface monitoring device comprising an adhesive patch and a first sensor and a second sensor configured to collect spontaneous patient swallow data, wherein collecting spontaneous patient swallow data further comprises audio data and tissue acceleration data associated with the spontaneous patient swallowing;
    transmitting the collected spontaneous patient swallow data to a computing device from the patient interface monitoring device;
    analyzing the spontaneous patient swallow data with a data analyzer at a processor of the computing device to identify spontaneous patient swallow events;
    counting a number of identified spontaneous swallow events over a predetermined time period;
    determining the spontaneous patient swallow frequency on the computing device based upon the number of identified swallow events over the predetermined time period;
    comparing, at the processor, the determined spontaneous patient swallow frequency to reference data, wherein the reference data comprises a plurality of model swallow data representative of a model swallow event based on patient parameters, the patient parameters including at least one of an age or a sex of the patient;
    generating, at the processor, a patient diagnosis of dysphagia based upon the comparison of the determined spontaneous patient swallow frequency to the reference data; and
    reporting results including the patient diagnosis of dysphagia, to a user of the computing device.

2. The method of claim 1, wherein the patient interface monitoring device adheres to the patient's neck.

3. The method of claim 1, wherein transmitting the collected spontaneous patient swallow data comprises wirelessly transmitting the spontaneous patient swallow data from the patient interface to the computing device.

4. The method of claim 1, wherein reporting the results further comprises outputting the determined spontaneous patient swallow frequency.

5. The method of claim 1, wherein the sensor of the patient interface monitoring device comprises an accelerometer that is configured to sense accelerations associated with movement of patient tissue when the patient swallows spontaneously.

6. The method of claim 2, wherein the patient interface monitoring device comprises a thin flexible polymeric substrate with a circular outer periphery and electronic components positioned at a center of the patient interface, the thin flexible polymeric substrate comprises a layer of adhesive that enables the device to adhere to the patient's neck, and the electronic components comprise a microprocessor configured to transmit the collected spontaneous patient swallow data to the computing device.

7. The method of claim 6, wherein the patient interface monitoring device is configured as a one-time-use patch that is applied to the patient's skin.

8. The method of claim 5, wherein analyzing the spontaneous patient swallow data comprises:
    comparing, at the data analyzer, a spontaneous patient swallow feature with one or more model swallow data representative of a model swallow event to determine a likelihood of the spontaneous patient swallow feature is a spontaneous patient swallow event, the model swallow data comprising at least one of acceleration data or pressure data; and
    incrementing, at the data analyzer, the number of identified swallow events in response to determining that the likelihood exceeds a threshold.

9. The method of claim 1, further comprising:
    comparing, using the computing device, the patient swallow frequency to reference data; and,
    outputting a result of comparing the spontaneous patient swallow frequency to the reference data, the result including the diagnosis.

10. The method of claim 1, further comprising attaching the patient interface monitoring device at a point over a lateral border of a trachea immediately inferior to a cricoid cartilage of the patient.

* * * * *